United States Patent [19]

Moosavian

[11] Patent Number: 4,610,768

[45] Date of Patent: Sep. 9, 1986

[54] LACTAM PURIFICATION

[75] Inventor: Seid H. Moosavian, Akron, Ohio

[73] Assignee: The Firestone Tire & Rubber Company, Akron, Ohio

[21] Appl. No.: 803,752

[22] Filed: Dec. 2, 1985

[51] Int. Cl.$^4$ .................. B01B 3/36; C07D 201/16
[52] U.S. Cl. ..................... 203/14; 540/540; 540/451; 546/243; 548/555
[58] Field of Search ............. 260/239.3 A; 546/243; 548/555; 203/14

[56] References Cited

U.S. PATENT DOCUMENTS 3,462,417  8/1969  Simmrock et al. .......... 260/239.3 A

Primary Examiner—Robert T. Bond
Attorney, Agent, or Firm—Daniel N. Hall

[57] ABSTRACT

A process for drying lactams to extremely low water contents is provided which comprises mixing the lactam with hydrocarbon distilling from the mixture a water/hydrocarbon vapor and or condensate, contacting said vapor or condensate with a drying agent to remove water and returning the dried distillate to the mixture to permit recycling process is capable of providing anionic polymerization grade lactam with a water content of less than about 50 ppm.

13 Claims, No Drawings

LACTAM PURIFICATION

This invention relates to a method for purifing caprolactam and other lactams of 5-12 ring members. More particularly, it is directed to a method for reducing the moisture content of such lactams comprising an extractive distillation in which the distillate is contacted with desiccant and then recycled. The ultra dry lactams produced are useful as polymerization monomers.

BACKGROUND OF THE INVENTION

Caprolactam and other lactams are widely used in the chemical industry as monomers for the preparation of homo- and copolmyers such as the well-known nylons. For a review, see the chapter "Lactams" by F. Millich and KV Seshadri in *Cyclic Monomers*, edited by Kurt C. Frisch, Wiley-Interscience publishers, New York, New York (1969), pages 179–311. Such lactam monomers can be polymerized by various mechanisms such as condensation, cationic and anionic polymerization processes. For maximum polymerization efficiency, particularly in anionic polymerization, the lactam monomer should be highly pure and virtually free of contaminants. If it is not, contaminants can interfere with the polymerization, catalyst and process thus severely limiting both the yield and molecular weight of the polymer. Anionic polymerization grade caprolactam should contain a minimum of contaminants and particularly a minimum of water. Water is a potent poison in anionic polymerization because it reacts with catalysts, such as alkyl lithiums, and terminates "living" polymer chains. Because of its polar nature and broad solvent power, caprolactam persistantly contains water, and freeing it of water to the desired polymerization grade levels is technically, and especially economically, a difficult task.

A number of techniques have been described in the literature for the purification and particularly the removal of water from lactams, such as caprolactam. See, for example, the previously cited "Lactams" pages 236–241. Specific examples include U.S. Pat. No. 3,170,592 which discloses a process for purification of caprolactam in benzene solution by successive counter current washings with aqueous lactam solutions. The impurities in the benzene solution pass into the aqueous solution and provide an organic lactam solution free of salts, acids and alkalies. U.S. Pat. No. 3,156,683 discloses purification of lactams by refluxing at reduced pressure while passing inert gas through the lactam to remove volatile purities and then distilling the purfied lactam. U.S. Pat. No. 3,145,198 discloses the purification of lactam by a series of steps comprising alkaline treatment, distillative reduction and oxidation. U.S. Pat. No. 2,786,052 discloses purification of lactams by passing hydrogen through an aqueous solution thereof in the presence of a catalyst, while U.S. Pat. No. 3,154,540 describes lactam purification by treatment with active metal preparations, such as the combination of zinc, dust and Raney nickle. British Pat. No. 1,530,357 describes purification of lactams by extraction with aqueous base of a toluene solution of the lactam. Crystallization provides purified lactam from the toluene solution. U.S. Pat. No. 3,755,305 describes purification of caprolactam by a combination of extraction and recrystallization combined with vacuum distillation. U.S. Pat. No. 3,676,431 describes a "conventional" process comprising extraction with an aromatic liquid such as benzene, followed by stripping and distillation. U.S. Pat. No. 3,792,045 discloses crystal extraction of a lactam with a solvent, such as pentane or decane, followed by distillation. There is nothing in this process relating to water removal and, indeed, water in the form of steam, is added at several stages without regard for the moisture content of the ultimate product. U.S. Pat. No. 3,904,609 describes treatment of a solution of lactam in a phenol-like solvent, followed by crystallization, wherein the crystals are washed in hexane, filtered and vacuum dried. U.S. Pat. No. 4,148,793 describes lactam purification by distillation in the presence of water and followed by water removal through distillation from the lactam. No recyling or regeneration of solvent is described. U.S. Pat. No. 4,239,682 describes extraction of a toluene solution of caprolactam. U.S. Pat. No. 3,839,324 discloses solvent distillation of raw lactam and crystal extraction with a nonaromatic solvent, followed by distillation including regeneration and recycling. No attention is paid to water content, but it appears that water or steam are added during the multistage process.

The abstract of Belgium Pat. No. 773,264 describes lactam purification with a hydrocarbon solvent such as hexane followed by vacuum drying or distillation under an inert gas.

A variety of organic chemicals are often desired for anionic polymerization or other processes, in a dry or anhydrous form. It is not surprising that a number of processes have been reported to accomplish such drying. U.S. Pat. No. 2,695,867 describes drying of an organic compound by azeotropic distillation with a hydrocarbon, such as benzene or hexane, but includes no mention of caprolactam. U.S. Pat. No. 3,575,818 describes a process for the production of absolute ethanol (that is, dry ethanol) using pentane, while U.S. Pat. No. 4,379,025 describes the removal of water from butylene oxime with an organic C7-9 carbon atoms solvent.

The need for absolutely dry anhydrous caprolactam has been recognized as shown by the previously cited "Lactams" and *Kirk Othmer Encyclopedia of Chemical Technology*, Volume 18, "Polyamides (caprolactam)," John Wiley & Sons NY, (1982), page 432. Therein it is stated: "Anhydrous caprolactam is produced and supplied for use in anionic polymerization processes" (p. 432). The subsequent discussion, however, does not indicate how such anyhdrous material is made or its water content is measured. For the purposes of this invention, anhydrous or dry caprolactam (and its homologs) is considered to contain less than 50 parts per million (weight/weight) water as measured by the Karl Fischer or Micheler's Ketone technique.

SUMMARY OF THE INVENTION

The present invention provides a process for making dry, anionic polymerization-grade unsubstituted 5-12 membered ring lactams which includes the steps of (a) distilling a mixture of (i) lactam and (ii) at least one hydrocarbon solvent having 5-12 carbon atoms to produce a water/hydrocarbon containing vapor; (b) optionally in condensing this vapor to form a condensate; (c) contacting said vapor and condensate with a drying agent to dry it and then returning the vapor and condensate to the mixture. Such distillation, drying and vapor/condensate return are continued until the water content of the lactam/hydrocarbon mixture is reduced to a level less than about 50 ppm. The dry, anionic polymerization-grade lactam can then be recovered by any number of conventional techniques such as evaporation, recrystallization and the like. Alternatively, the solution of caprolactam and diluent solvent is used directly for anionic polymerization or copolymerization usually by anionic catalysis.

The inventive process prepares an anionic polymerization grade of caprolactam or other high boiling lactam containing less than about 50 ppm water, typically less than 30 ppm water and characteristically less than 10–30 ppm water. Such anionic polymerization grade lactams can be used in the production of polymers by anionic polymerization techniques such as those described in the above-cited "Cyclic Monomers" and in *Journal of Polymer Science*, Vol. 12 pages 2613–2622, (1974), by Hergenrother and Ambrose and the references cited therein. These disclosures are hereby incorporated by reference for their descriptions of anionic polymerization in general and specifically for their description of the synthesis of polybutadiene-nylon-6 and polystyrene-nylon-6.

DETAILED DESCRIPTION OF THE INVENTION

Technical, commercial grade caprolactam has a water content of about 0.1–0.5% (1,000–5,000 ppm). Since such moist caprolactam is not suitable for anionic polymerization because of both of the catalyst and premature chain termination, techinques for drying caprolactam and homologous lactams with 5–12 ring members are desirable. In the present invention, the caprolactam (or other lactam) is dissolved in hydrocarbon with mild heat and agitation to form a mixture which is usually a clear solution. Typically, the hydrocarbon solvent used is normally a liquid hydrocarbon containing 5–12 carbon atoms. In an efficient embodiment, the solvent can be used as diluent in subsequent anionic polymerization or copolymerization of caprolactam. Aliphatic hydrocarbons such as normal alkanes are examples of solvents that can be used in both the process of this invention and subsequent anionic polymerization of the purified lactam monomer. Generally, the solvent used in this invention is an aliphatic compound or mixture of such aliphatic compounds such as hexane, heptane, octane, mixtures thereof or the various commercial aliphatic solvents such as: gasoline, naphtha, kerosine, varasol and the like. A convenient hydrocarbon solvent is commercial hexane. Thus aliphatic hydrocarbons, including mixtures thereof, having boiling points in the range of about 10°–200° C. are typically useful.

The solvent lactam mixture generally has a composition of 10–75 parts (by weight) lactam to 90–25 parts (by weight) solvent.

The moisture-removing, drying, desiccating process can be conveniently carried out in a batchwise or a continuous manner. In the batchwise process, the lactam/hydrocarbon solution is distilled at or near atomospheric pressure, and provision is made for transport of the vapor produced to a bed of drying agent.

In the continuous process, provision is made for regenerating the drying agent while it is in the drying bed. This may be done by temporarily interrupting the flow of lactam to the bed while the bed is purged with gas and optionally heated to remove water and thus regenerate the drying agent's dessicant properties. In another embodiment, dual parallel drying beds are used alternately. While one is being used, the other is being dried. When the first begins to lose its drying capacity, the lactam vapor or condensate is diverted to the second and the first then dried. Such continuous operations with dual beds are known chemical processing techniques.

It is also possible to conduct the drying process in a multistage manner in which the vapor or condensate is passed through a series of drying beds that progressively produce drier and drier effluant after each stage. Two, three, four or more stages can be used with beds of the same or different drying agents in each as desired. Techniques for carrying out such sequential multistage operations are known and can be adapted to the practice of this invention with the knowledge gained from the present disclosure. The following description applies to both batchwise and continuous drying embodiments of the invention.

Usually the solvent vapor, carrying impurities including water is purified by going through a condenser to form condensate, though this is not essential to the invention. The vapor and condensate (if any) are contacted with a dry agent, dried and then passed to a return line. The desiccated vapor and condensate are returned to the solvent-lactam reservoir. Thus recycling of dried solvent is established and maintained for as long as is necessary to reach the desired low concentration of water in the lactam/hydrocarbon mixture. Normally the recycle period is about one to about ten hours.

Provision may also be made for taking samples either before or after the drying operation, and provision is made for supplying heat to the solvent-lactam mixture reservoir to maintain boiling. The drying operation is conducted in a convenient, conventional manner. Many suitable drying agents and techiques are known. See, for example, Kirk-Othmer, *Encyclopedia of Chemical Technology*, Vol. 8, "Drying Agents," John Wiley & Sons, New York, New York (1979). Among the useful drying agents are alumina, silica and molecular sieves which are known to absorb water from hydrocarbon vapor and condensates. Alumina that is activated, that is, dried by heating to a low moisture content, is well-known and useful. The techniques, materials and relative amounts of drying agent used are all conventional and well-known to those of skill in the art as shown by Kirk-Othmer "Drying Agents" which is incorporated by reference herein for its relevant disclosures in this regard. The period of recycle naturally depends on the reflex temperature and the amounts of solvent and drying agent and the dimensions of the equipment. Normally, however, when hexane is used in the amounts indicated above in appropriate sized equipment, recycle times of about two to eight hours are sufficient. The progress of moisture removal from the vapor/condensate can be easily determined by sampling the returning condensate after it has left the drying agent column and determining the moisture content thereof, through any number of convenient techniques such as the Karl-Fischer technique or the Micheler Ketone determination. A number of automated techniques for moisture determination are also known. Normally the drying agent itself is activated, dried or regenerated by heat according to conventional techniques as necessary.

Often the drying steps are repeated either batchwise or continuously until the water content of the lactam/hydrocarbon mixture is about 2–50 ppm water as determined by the above-described techniques. Recovery of the lactam by conventional techniques such as evaporation of solvent, crystallization etc., from the dried lactam/hydrocarbon mixture then provides an anionic polymerization grade lactam, such as caprolactam, having a water content of 50-10 ppm water.

EXAMPLE (BEST MODE)

A mixture is prepared of 300 parts (by weight) caprolactam flake (having a moisture content of 600-800 ppm) and 300 parts (by weight) hexane. This mixture is placed in a round reservoir, fitted with a vapor column, connected to a water condenser and a desiccant column containing 100 parts per 100 parts of caprolactam (by weight) molecular sieve (3A obtained from Linde Company, a division of Union Carbide.) The sieve is reactivated by heating to 300°-450° F. before use. In continuous operation, this reactivation can be done intermittently when needed. The mixture is distilled and the hexane condensated, passed through the sieve bed and the dried hexane condensate issuing from the drying operation returned to the reservoir for a total period of approximately two hours. The distillation temperature is found to be approximately 155°-180°F. Moisture content of dried condensate is determined by Micheler Ketone technique. Table I shows the results of these moisture determinations on various samples. The caprolactam recovered by removal of the hexane from the reservoir has a moisture content of 13 ppm and is suitable for use in anionic copolymerizations with butadiene or styrene catalyzed by butyl lithium.

TABLE I

| Sample | Sample Description | ppm $H_2O$ Impurities |
|---|---|---|
| A | Caprolactam after hexane extract (5 hours). | 15* |
| B | Recovered solvent | 27 |
| C | Caprolactam after hexane extraction 10 hours. | 13 |
| D | Recovered solvent after 10 hours. | 9 |

*Flake raw caprolactam 600-800 before drying

Conditions

1. Distillation temperature—157°-180°
2. Hexane-caprolactam wt. ratio—1/1
3. Molecular seive regeneration at 300°-500° F. for 4 hours.

This practice of the invention in this Example reduces the water content of the lactam from 600-800 ppm to 15-13 ppm after about 5-10 hours.

What is claimed is:

1. A process for drying unsubstituted 5-12-membered ring lactams comprising the steps of:
    (a) mixing (i) lactam with (ii) at least one hydrocarbon of 5-12 carbon atoms to form a mixture;
    (b) distilling said hydrocarbon from the misture to produce a water/hydrocarbon-containing vapor and/or water/hydrocarbon-containing condensate;
    (c) contacting said vapor and/or condensate with a drying agent so that water is removed from it;
    (d) returning the dried distillate to the mixture;
    (e) repeating steps (b)-(d) until the water content of the lactam/hydrocarbon mixture is less than about 50 ppm water;
    (f) recovering the lactam in a dried form having a water content less than about 50 ppm water.
2. A process as claimed in claim 1 wherein (a) the wet lactam has a water content of about 500-1000 ppm water.
3. A process as claimed in claim 2 wherein (b) a water/hydrocarbon-containing condensate is produced.
4. A process as claimed in claim 3 wherein (a) the hydrocarbon is an aliphatic hydrocarbon having a boiling point (at atmospheric pressure) of about 10°-200° C.
5. A process as claimed in claim 4 where (a) the hydrocarbon is hexane, heptane, octane or a mixture thereof.
6. A process as claimed in claim 2 wherein (c) the drying agent is activated alumina, silica or a molecular sieve capable of absorbing water.
7. A process as claimed in claim 5 wherein (c) the drying agent is activated alumina, silica or a molecular sieve capable of absorbing water.
8. A process as claimed in claim 2 wherein (e) steps (2)-(4) are repeated until the water content of the lactam/hydrocarbon mixture is about 20-50 ppm water.
9. A process as claimed in claim 7 wherein (e) steps (2)-(4) are repeated until the water content of the lactam/hydrocarbon mixture is about 20-50 ppm water.
10. A process as claimed in claim 2 wherein (a) the lactam is caprolactam.
11. A process as claimed in claim 9 wherein (a) the lactam is caprolactam.
12. Anionic polymerization grade caprolactam having a water content of about 50-10 ppm water made by the process of claim 11.
13. A process as claimed in claim 2 wherein (a) the drying step (c) is carried out continuously.

* * * * *